US012742778B2

(12) United States Patent
Reichberg

(10) Patent No.: US 12,742,778 B2
(45) Date of Patent: Sep. 22, 2026

(54) TEST TO PREDICT AND EVALUATE INNATE IMMUNE RESPONSES TO INFECTIONS AND METHODS OF TREATMENT THEREOF

(71) Applicant: Samuel B. Reichberg, Hartsdale, NY (US)

(72) Inventor: Samuel B. Reichberg, Hartsdale, NY (US)

( * ) Notice: Subject to any disclaimer, the term of this patent is extended or adjusted under 35 U.S.C. 154(b) by 0 days.

(21) Appl. No.: 17/980,235

(22) Filed: Nov. 3, 2022

(65) Prior Publication Data

US 2023/0135111 A1 May 4, 2023

Related U.S. Application Data

(60) Provisional application No. 63/275,244, filed on Nov. 3, 2021.

(51) Int. Cl.
*G01N 33/569* (2006.01)
*A61K 38/21* (2006.01)

(52) U.S. Cl.
CPC ........... *G01N 33/569* (2013.01); *A61K 38/21* (2013.01); *G01N 2333/42* (2013.01); *G01N 2800/26* (2013.01)

(58) Field of Classification Search
CPC ........... G01N 2333/42; G01N 2800/26; G01N 33/569; A61K 38/21
See application file for complete search history.

(56) References Cited

U.S. PATENT DOCUMENTS 9,005,902 B2 4/2015 Lalvani et al.
2013/0034844 A1* 2/2013 Boyle ..................... A61P 37/02 435/5

FOREIGN PATENT DOCUMENTS

JP 2014221795 A * 11/2014 ......... A61K 39/3955
WO 2010/009494 A1 1/2010
WO 2017/164659 A2 9/2017
WO WO-2017164659 A3 * 9/2018 ......... G01N 33/5008

OTHER PUBLICATIONS

Imahara, Scott D et al. “The influence of gender on human innate immunity.” Surgery vol. 138,2 (2005): 275-82. doi:10.1016/j.surg.2005.03.020 (Year: 2005).*
University of Michigan Pathology Handbook, Cryoglobulin Follow-up Monoclonal Gammopathy Evaluation, 2001. https://www.pathology.med.umich.edu/handbook/#/details/5289University%20of%20Michigan%20Pathology%20handbook%202001 (Year : 2001).*
Negorev, Dmitri et al. Human neutrophils can mimic myeloid-derived suppressor cells (PMN-MDSC) and suppress microbead or lectin-induced T cell proliferation through artefactual mechanisms. Scientific Reports vol. 8, 1 (2018). https://doi.org/10.1038/s41598-018-21450-6 (Year: 2018).*
Mellstedt, H. “In vitro activation of human T and B lymphocytes by pokeweed mitogen.” Clinical and experimental immunology vol. 19,1 (1975): 75-82. (Year: 1975).*
Malin Jakob et al. “Remdesivir against COVID-19 and Other Viral Diseases” Clinical Microbiology Reviews vol. 34, 1 (2020). https://doi.org/10.1128/cmr.00162-20 (Year: 2020).*
Shishido, Stephanie et al. “Humoral innate immune response and disease” Clinical Immunology vol. 144 2 (2012). https://doi.org/10.1016/j.clim.2012.06.002. (Year: 2012).*
Tanaka, Toshio et al. “Interleukin (IL-6) Immunotherapy.” Cold Spring Harbor perspectives in biology vol. 10,8 a028456. Aug. 1, 2018, doi:10.1101/cshperspect.a028456 (Year: 2018).*
Kawai, Toro et al. “Innate immune recognition of viral infection” Nature Immunology vol. 7 2 (2006). https://doi.org/10.1038/ni1303 (Year: 2006).*
Jacobs, Evan et al. “Cytokines Elevated in HIV Elite Controllers Reduce HIV Replication In Vitro and Modulate HIV Restriction Factor Expression” Journal of Virology vol. 91 6 (2017). https://doi.org/10.1128/jvi.02051-16 (Year: 2017).*
Page, Andrea V, and W Conrad Liles. “Granulocyte colony-stimulating factor, granulocyte-macrophage colony-stimulating factor, and other immunomodulatory therapies for the treatment of infectious diseases in solid organ transplant recipients.” Current opinion in organ transplantation vol. 13,6 (2008) (Year: 2008).*
Ramshaw, I A et al. “Cytokines and immunity to viral infections.” Immunological reviews vol. 159 (1997): 119-35. doi:10.1111/j.1600-065x.1997.tb01011.x (Year: 1997).*
Grumolato, L., et al., “Canonical and noncanonical Wnts use a common mechanism to activate completely unrelated coreceptors,” *Genes Dev*. Nov. 15, 2010, 24, 22, 2517-2530.
Huang, X., et al., “Genome editing abrogates angiogenesis in vivo,” *Nat Commun*. Jul. 24, 2017, 8, 1, 112.
Johnson, M.C., and Kamm, R.D., “The role of Schlemm’s canal in aqueous outflow from the human eye,” *Invest Ophthalmol Vis Sci*. Mar. 1983, 24, 3, 320-325.
Kamizaki, K., et al., “Ror2 signaling regulated by differential Wnt proteins determines pathological fate of muscle mesenchymal progenitors,” *Cell Death and Disease*, 2024, 15, 784.
Keller, K. E., et al., “Consensus recommendations for trabecular meshwork cell isolation, characterization and culture,” *Experimental Eye Research*, 2018, 171, 164-173.

(Continued)

*Primary Examiner* — Gregory S Emch
*Assistant Examiner* — Mckenzie A Dunn
(74) *Attorney, Agent, or Firm* — McCarter & English, LLP

(57) ABSTRACT

Disclosed herein are methods of determining innate immune response to infections of a subject comprising mixing a subject blood sample comprising plasma with an anticoagulant solution; adding a sample of innate immune cells incubated with one or more stimulants to the mixture to form a cell sample aliquot; incubating the cell sample aliquots with and without the stimulants for at least one hour at an optimal temperature; separating the plasma from the innate immune cells in the aliquot; measuring one or more cytokines in the plasma; calculating a net stimulation of cytokines the cell sample aliquot; and comparing the net stimulation to a reference group of subjects having adequate innate immunity reactivity. Also disclosed are methods of treating a subject having an innate immune response to an infection.

17 Claims, 2 Drawing Sheets

(56) References Cited

OTHER PUBLICATIONS

International Search Report of the International Searching Authority mailed on Feb. 9, 2023, issued in connection with International Application No. PCT/US22/48838 (4 pages).
Written Opinion of the International Searching Authority mailed on Feb. 9, 2023, issued in connection with International Application No. PCT/US22/48838 (6 pages).
Guo, et al., "The Rat Antigen-Presenting Lectin-Like Receptor Complex Influences Innate Immunity and Development of Infectious Diseases," Genes and Immunity (2009), https://www.nature.com/articles/gene20094 (10 pages).
Nowell, "Phytohemagglutinin: an Initiator of Mitosis in Cultures of Normal Human Leukocytes," Cancer Research, vol. 20, Issue 4, May 1, 1960 (24 pages).
Chen, et al., "IP-10 and MCP-1 as Biomarkers Associated with Disease Severity of COVID-19," Moleduar Medicinbe (2020) (12 pages).
Voloudakis, et al., "A Translational Genomics Approach Identifies IL 10RB as the Top Candidate Gene Target for COVID-19 Susceptibility," Genomic Medicine (2022) (15 pages).
Riss, et all, "Cell Viability Assays," Eli Lilly & Company and the National Center for Advancing Translational Sciences (2004) (26 pages).

* cited by examiner

Incubate at 37 °C for 16-24 hours

Separate blood plasma by centrifugation

Transfer to measurement containers

TEST TO PREDICT AND EVALUATE INNATE IMMUNE RESPONSES TO INFECTIONS AND METHODS OF TREATMENT THEREOF

CROSS-REFERENCE TO RELATED APPLICATION

The present application claims priority under 35 U.S.C. § 119(e) to U.S. Provisional Patent Application No. 63/275,244, filed Nov. 3, 2021, which is incorporated herein by reference in its entirety.

FIELD

The present disclosure relates to methods of predicting immune response to infections in order to diagnose the cause of the infection, predict its course, and determine methods of treating or preventing such infections.

BACKGROUND

Currently substances that are specific to a pathogenic microorganism are added to a patient blood sample to stimulate immune cells to induce the secretion of interferons and other cytokines through the activation of the adaptive immune system. These laboratory tests currently in use have been designed to aid in the diagnosis of infections caused by specific microbes, including tuberculosis and COVID-19, as well as to identify specific targets of autoimmune diseases (e.g., the QuantiFERON®-TB Gold In-Tube and the T-SPOT®.TB (T-Spot) tuberculosis diagnostic tests [6]).

The innate immune system plays an important role in limiting viral invasion in early infection, as demonstrated by the severity of SARS-CoV-2 infections in patients with genetic deficiencies that affect the innate immune system and the reduced COVID-19 severity in patients with activated innate immune systems following other viral infections. Early identification of subjects who will likely develop severe disease due to weak innate immunity would allow selective recommendations for more stringent protection against infection and, if the person does get infected, to promptly initiate pharmaceutical prophylaxis, such as monoclonal antibody, anti-viral drugs or interferon administration. These medications are generally effective only in the early stages of infection, at a time when predicting its clinical evolution is difficult. Conversely, most individuals who are not expected to develop severe disease can be subject to less stringent epidemic mitigation measures and can avoid pharmacological prophylaxis that is scarce and can cause side effects.

Here, Applicant repurposes as an independent test one of the components of these specific diagnostic procedures hereto used as an internal control. In its current quality control role, confirmation of the ability of lectins to induce secretion of interferon or other cytokines above a threshold is used as an indicator of the suitability of the blood sample to test it for the presence of adaptive immunity to a specific infectious agent.

SUMMARY

The present disclosure relates to a new laboratory test that uses non-specific, maximum stimulation of immune blood cells in samples taken from an individual by adding plant carbohydrate-binding proteins called lectins or similar general stimulatory substances, and subsequent measurements of the level of interferon or other cytokines secreted by these cells after stimulation, in order to assess the capacity of the innate immune system to counteract invasion by a variety of infectious agents, including the SARS-CoV-2 virus. As in other laboratory tests, the inverse relationship of the concentrations of the secreted cytokines with subsequent disease severity will be defined by clinical studies. If confirmed by these studies, results from this test can inform prevention when performed before infection or prophylaxis when performed early after infection.

The relationship between infection and disease is variable. The same infectious agent can produce few or no symptoms in some patients and can cause severe symptoms, or even the demise, of others. This is particularly the case for SARS-CoV-2, the coronavirus that causes the COVID-19 pandemic. Only roughly 2.5-5% of unvaccinated persons end up with a disease that requires hospitalization and less than 1% die as result of their first SARS CoV-2 infection. Currently, while general determinants of COVID-19 severity, such as age, gender, obesity, hypertension, and diabetes are well known, these conditions affect large segments of the population, and their presence cannot accurately predict the severity of disease in specific patients. The novel clinical test described here has the potential to provide such predictive information.

Protection against infection in persons who had not previously or recently been exposed to a specific infectious agent mostly relies on the person's innate immune system because they have not yet developed, or have decreased, adaptive immunity which is primarily mediated by specific antibodies and primed immune cells. The present disclosure covers a simple blood test to evaluate the strength of a person's innate immune system, as well as the adaptive immune system. It can identify, and in some embodiments, treat patients at risk for severe disease that would benefit from enhanced mitigation measures and prophylaxis. Focusing preventive treatments, such as interferon, specific anti-viral drugs or monoclonal antibody administration on these patients would significantly improve drug utilization and effectiveness while sparing those who would only develop mild disease enhanced social distancing and prophylactic interventions, such as antiviral drugs and therapeutic antibody infusions. In some embodiments, patients identified as being at risk for severe disease are treated, e.g., with antibiotics, antiviral drugs, donor and monoclonal antibodies and/or interferons.

Lymphocytes constitute about one-third of the blood white cells. They are smaller than other blood white cells are mainly comprised of cell nucleus and very little cytoplasm. These characteristics and the lack of obvious activity in the blood contributed to their early description as cells that have reached the final stage of differentiation (terminally differentiated) analogous to red blood cells. However, in 1960 Nowell [1] discovered that lymphocytes undergo rapid transformation, increasing their cytoplasm and starting to multiply, in the presence of phytoaggulutinin (PHA), a bean lectin that binds to red cells and agglutinates them, hitherto used in the laboratory to investigate red cell blood groups and as a tool to separate red from white cells. Shortly thereafter, in 1965 PHA was found to also stimulate the secretion by lymphocytes of interferon before they start multiplying [2]. Other, but not all, lectins also stimulate lymphocyte cytokine secretion and proliferation. Since then, PHA and other lectins have become a main scientific tool of immunology and have been used in in vitro diagnostic testing. The best known clinical laboratory use of lectins is as a control in clinical diagnostic bioassays that detect cellular immunity to specific substances, including pathogenic microorganisms and auto antigens which are added to blood samples to stimulate lymphocytes previously exposed to these microorganisms by the infection. In the absence of these antigens, lectins confirm the vitality and ability of the blood sample lymphocytes to react and, thus allows the interpretation of the lack of response to the added antigens to absence of immunity rather than merely cell damage during the processing and transport of the blood sample.

Thus, maximum stimulation of immune blood cells in a blood sample by lectins or other chemicals and subsequent measurement of the amounts of cytokines, such as interferons, they produce after stimulation, has been in the role as an internal control for diagnostic bioassay tests primarily used to identify adaptive immune responses in the form of cellular activities that protect the organism against specific infectious agents, or attack tissues that contain the autoantibodies present in autoimmune disease. The new use described here comprises (i) predicting the general ability of the person or animal immune system to react to infections; (ii) predicting the effectiveness of early preventive pharmaceutical interventions to decrease disease severity, (iii) monitoring the evolution of infection severity, and in other medical uses where evaluating the general capacity of the innate, rather than the adaptive, immune system, is pertinent.

One aspect of the present disclosure is thus for a method of determining innate immune response to infections of a subject comprising: (a) mixing a subject blood sample comprising plasma with an anticoagulant solution; (b) adding a sample of innate immune cells incubated with one or more stimulants to the mixture of step (a) to form a cell sample aliquot; (c) incubating the cell sample aliquot for at least one hour at an optimal temperature; (d) separating the plasma from the innate immune cells in the aliquot; (e) measuring one or more cytokines in the plasma; (f) calculating a net stimulation of cytokines the cell sample aliquot; and (g) comparing the net stimulation to a reference group of subjects having adequate innate immunity reactivity.

In some embodiments, the optimal temperature is in a range of about 36.1° C. to about 37.2° C. In some embodiments, wherein the one or more cytokines are one or more interferons, one or more interleukins, one or more tumor necrosis factors, one or more chemokines, one or more lymphokines, or a combination thereof; and in some embodiments, the one or more interferons are IFN-α, INF-β, INF-γ, IFN-ε, IFN-κ, IFN-ω, IFN-δ, IFN-τ, IFN-ζ, INF-λ, or a combination thereof. In some embodiments, the one or more stimulants are one or more lectins; and in some embodiments, the one or more lectins are phytohemagglutinin, concanavalin A, lentil lectin, snowdrop lectin, ricin, peanut agglutinin, jacalin, hairy vetch lectin, wheat germ agglutinin, elderberry lectin, *Maakia amurensis* leukoagglutinin, *Maakia amurensis* hemagglutinin, *Ulex europaeus* agglutinin, *Aleuria aurantia* lectin, or a combination thereof. In some embodiments, the one or more stimulants is pokeweed mitogen. In some embodiments, the method comprises the further step after step (a) and before step (b) of dividing the mixture of step (a) into a second mixture and adding a sample of stimulant-free innate immune cells to the second mixture to form a control cell sample aliquot; and in some embodiments, step (f) comprises comparing the measurement of the one or more cytokines in the plasma of the cell sample aliquot with a measurement of one or more cytokines in the plasma of the control aliquot.

Another aspect is for a method of treating a subject having an innate immune response to an infection comprising: (a) mixing a subject blood sample comprising plasma with an anticoagulant solution; (b) adding a sample of innate immune cells incubated with one or more stimulants to the mixture of step (a) to form a cell sample aliquot; (c) incubating the cell sample aliquot for at least one hour at an optimal temperature; (d) separating the plasma from the innate immune cells in the aliquot; (e) measuring one or more cytokines in the plasma; (f) calculating a net stimulation of cytokines the cell sample aliquot; (g) comparing the net stimulation to a reference group of subjects having adequate innate immunity reactivity; and (h) administering a therapeutic to a subject identified as having the innate immune response to the infection.

In some embodiments, the therapeutic is one or more cytokines, one or more antibodies, antivirals, or a combination thereof; in some embodiments, the one or more cytokines is one or more interferons, one or more interleukins, one or more tumor necrosis factors, one or more chemokines, one or more lymphokines, or a combination thereof; in some embodiments, the one or more interferons are IFN-α, INF-β, INF-γ, IFN-ε, IFN-κ, IFN-ω, IFN-δ, IFN-τ, IFN-ζ, INF-λ, or a combination thereof; in some embodiments, the one or more interleukins are IL-1, IL-2, IL-3, IL-4, IL-5, IL-6, IL-7, IL-8, IL-9, IL-10, IL-11, IL-12, IL-13, IL-14, IL-15, IL-16, IL-17, or a combination thereof; in some embodiments, the one or more tumor necrosis factors are TNFα, TNFβ, TNFγ, or a combination thereof; in some embodiments, the one or more chemokines are CCL14, CCL19, CCL20, CCL21, CCL25, CCL27, CXCL12, CXCL13, CXCL-8, CCL2, CCL3, CCL4, CCL5, CCL11, CXCL10, or a combination thereof; and in some embodiments, the one or more lymphokines is granulocyte-macrophage colony-stimulating factor. In some embodiments, the one or more antibodies are bamlanivimab plus etesevimab, casirivimab plus imdevimab, sotrovimab, tixagevimab plus cilgavimab, tocilizumab, or bebtelovimab. In some embodiments, the one or more antivirals are remdesivir, azithromycin, hemagglutinin inhibitor, nirmatrelvir with ritonavir, molnupiravir, or a combination thereof. In some embodiments, the optimal temperature is in a range of about 36.1° C. to about 37.2° C. In some embodiments, the one or more cytokines are one or more interferons, one or more interleukins, one or more tumor necrosis factors, one or more chemokines, one or more lymphokines, or a combination thereof; and in some embodiments, the one or more interferons are IFN-α, INF-β, INF-γ, IFN-ε, IFN-κ, IFN-ω, IFN-δ, IFN-τ, IFN-ζ, INF-λ, or a combination thereof. In some embodiments, the one or more stimulants are one or more lectins; and in some embodiments, the one or more lectins are phytohemagglutinin, concanavalin A, lentil lectin, snowdrop lectin, ricin, peanut agglutinin, jacalin, hairy vetch lectin, wheat germ agglutinin, elderberry lectin, *Maakia amurensis* leukoagglutinin, *Maakia amurensis* hemagglutinin, *Ulex europaeus* agglutinin, *Aleuria aurantia* lectin, or a combination thereof. In some embodiments, the one or more stimulants is pokeweed mitogen. In some embodiments, the method comprises the further step after step (a) and before step (b) of dividing the mixture of step (a) into a second mixture and adding a sample of stimulant-free innate immune cells to the second mixture to form a control cell sample aliquot; and in some embodiments, step (f) comprises comparing the measurement of the one or more cytokines in the plasma of the cell sample aliquot with a measurement of one or more cytokines in the plasma of the control aliquot.

DRAWINGS

DETAILED DESCRIPTION

Figure 1:
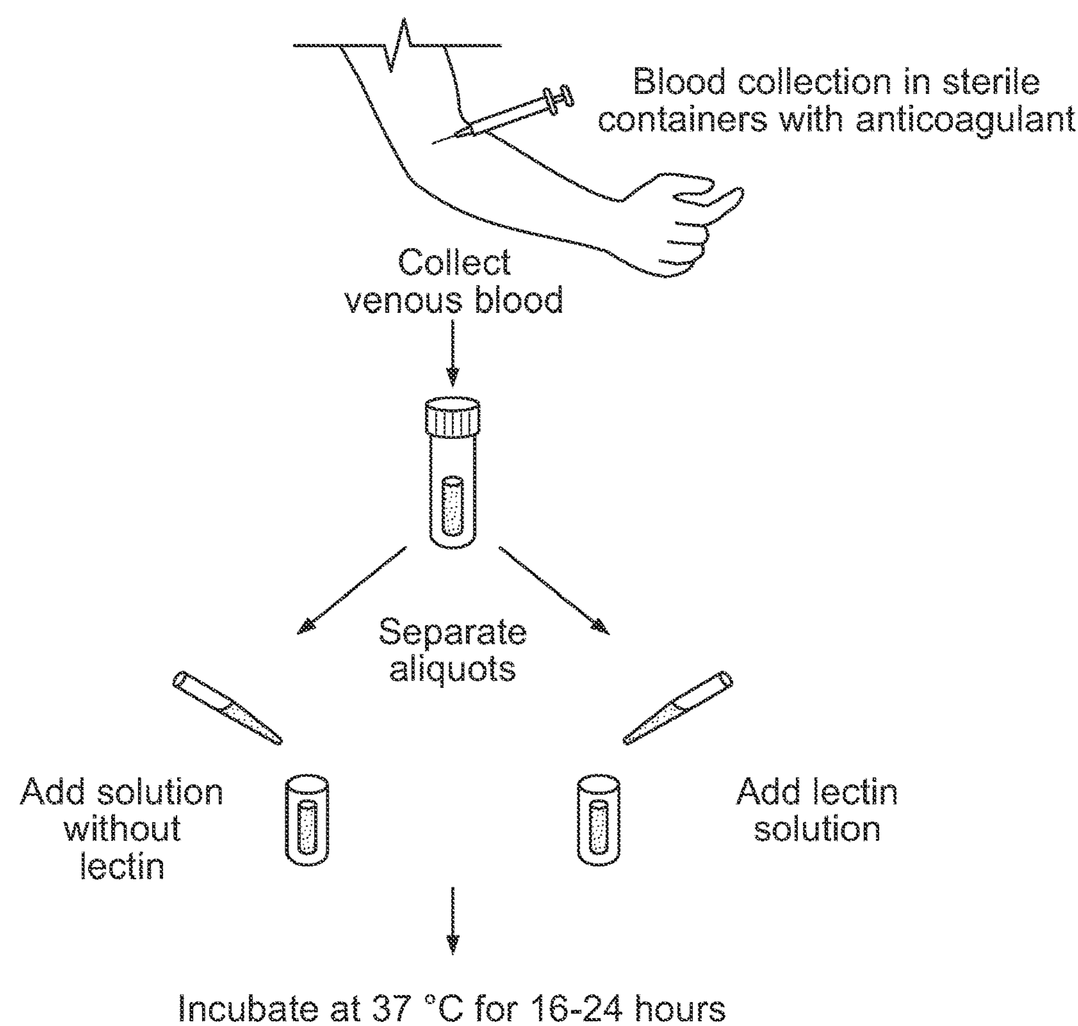
FIG. 1 shows a diagram of an embodiment of the present disclosure.
Figure 1:
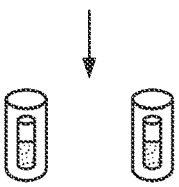
Figure 1:
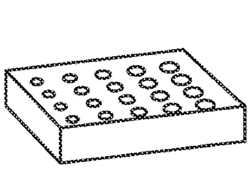
Figure 1:

Medical and Technical Aspects:

The concentration of cytokines in the body, including blood, is very small. For that reason, they are generally measured through their molecular effects on cells and body tissues using sophisticated sensitive research techniques. However, their concentration in blood increases several-fold after stimulation of immune cells in the blood by antigens, reaching levels measurable using standard clinical laboratory techniques. Currently, the most common application of this technique are assays patented for use in the diagnosis of tuberculosis (Interferon Gamma Release Assay and Elispot tests).

A blood sample is extracted from the individual's vein through a hypodermic needle and transferred onto a sterile tube containing materials that suppresses blood clotting and keeps the blood cells alive and vital. The sample is then incubated in the presence of molecules that are specific to the organism suspected of being the cause of the disease, such as proteins found only in *Mycobacterium tuberculosis*, the cause of tuberculosis, or the SARS CoV-2 virus proteins. After incubation for several hours at body's temperature, plasma, which is the fluid component of the blood, is separated from the cells and the concentration of cytokines produced is measured using a standard clinical laboratory procedure called immunoassay or other detection methods. In persons infected with the specific microbe being investigated, the cells that have been sensitized through infection by the microbe are stimulated by the specific proteins and respond by producing increased amounts of cytokines. Samples where the increase does not exceed a prescribed concentration threshold are considered to belong to uninfected individuals. In order to ensure the viability and vitality of the immune cells in the sample, instead of incubating them with the specific microbial molecules, aliquots are incubated with stimulants that cause a strong but non-specific stimulation of immune cells in the sample. The stimulants generally used are sugar-binding proteins of plant origin called lectins. Other stimulants include, e.g., pokeweed mitogen.

The lectin commonly used is phytohemagglutinin. It binds tightly to the surface of immune cells in a manner similar to the binding of specific microbial proteins, triggering secretion of interleukins by the immune cell as if they had been exposed to material from the targeted microorganism. Other lectins include, but are not limited to, concanavalin A, lentil lectin, snowdrop lectin, ricin, peanut agglutinin, jacalin, hairy vetch lectin, wheat germ agglutinin, elderberry lectin, *Maakia amurensis* leukoagglutinin, *Maakia amurensis* hemagglutinin, *Ulex europaeus* agglutinin, and *Aleuria aurantia* lectin. But not all have the same effect as phytohemagglutinin.

Cytokine amounts produced by stimulated blood cells vary widely, but they can be assessed against a single minimum threshold. However it is necessary to determine whether the cells in the sample can secrete cytokines to ensure that if the result of the test is a lack of response to specific microbial substances, it is not to sample cell damage or death but to the absence of infection history by the specific organism.

Role of the Innate Immune System in COVID-19:

As it is the case for other viruses, SARS-CoV-2 has the ability counteract host immunity defenses, by suppressing their production or damping their effects. Significant impairment of both innate and adaptive immune responses has been reported in elderly patients with severe COVID-19 late during infection, but the opposite takes place when severely affected patients suffer sharp increases in the inflammatory response recognized as the "cytokine storm".

In contrast to late immunologic phenomena, lesser is known about the influence of the strength of genetically intact innate immunity prior to, or early during infection, but the fundamental defensive role of cytokines such as interferons is suggested by the prevalence of severe COVID-19 in persons with auto-antibodies against interferons or associated genetic conditions, such as the correlation of interferon gamma inducible protein-10 (IP-10) with COVID-19 severity [3] and the upregulation of IL10RB, a member of the interferon cellular pathway, as the top candidate gene target for COVID-19 susceptibility [4].

The test described herein would not only facilitate early or prophylactic COVID-19 pharmaceutical interventions, but also clinical assessment at population scale of the influence of the immune system on pandemic severity.

Figure 2:
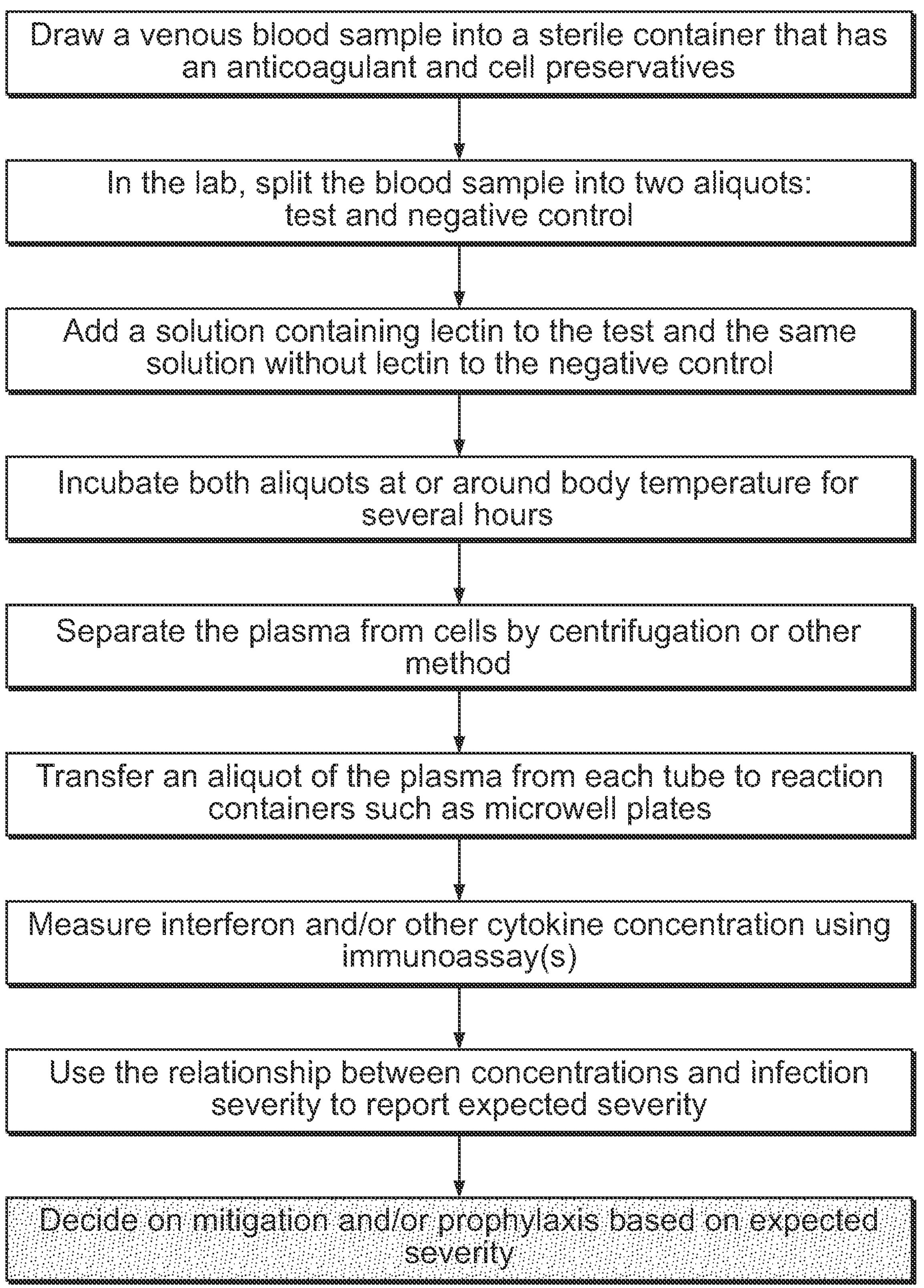
FIG. 2 shows a flow chart of an embodiment of the present disclosure.

Test and Treatment Procedures:

The test comprises, in some embodiments, 1) pouring a subject blood sample obtained using venipuncture into a sterile container and mixing it with an anticoagulant solution. (In order to distinguish between intrinsic decreases in the ability of lymphocytes to secrete interleukins and lack of cell viability due to damage to the cells, a general cell viability laboratory method [5] will be used.) 2) in some embodiments, dividing the blood sample into two aliquots: one for the performance of the test and another as a negative control, 3) adding a stimulant of innate immune cells to one aliquot and, in embodiments using a negative control, adding an equal volume of the same solution, but lacking the stimulant, to the other aliquot, 4) incubating the aliquot(s) at body or optimal temperature (in some embodiments, 36.1° C. to about 37.2° C.; in some embodiments, 37° C.) for several hours (in some embodiments about 16 to about 24 hours), 5) separating the plasma from the cells in the aliquot(s) by centrifugation or other methods, 6) measuring the concentration of interferon and/or other cytokines in the plasma using immunoassay or other methods, 7) calculating the net stimulation of the test aliquot by, e.g., subtracting the concentration of the cytokine in the control aliquot and, 8) reporting this net concentration alongside the lower value found in a reference group of subjects proven to have adequate innate immunity reactivity based on different method(s). See FIGS. 1 and 2 attached herewith for a diagram of these basic test steps.

In some embodiments, subjects identified as being at risk of disease, such as severe COVID-19, Influenza and Respiratory Syncytial Virus infections, are then treated (in some embodiments, prophylactically) with, e.g., antibiotics, antiviral medications, interferons and/or monoclonal antibodies.

Examples of interferons useful as a prophylactic or treatment for such subjects include, but are not limited to, IFN-α (e.g., 2a, 2b), INF-β (e.g., 1a, 1b), INF-γ (e.g., 1b), IFN-ε, IFN-κ, IFN-ω, IFN-δ, IFN-τ, IFN-ζ, INF-λ, and a combination thereof.

Other cytokines useful as prophylactic or treatment for such subjects include, but are not limited to, interleukins (e.g., IL-1, 2, 3, 4, 5, 6, 7, 8, 9, 10, 11, 12, 13, 14, 15, 16, 17), tumor necrosis factors (e.g., TNFα, TNFβ, TNFγ), chemokines (e.g., CCL14, CCL19, CCL20, CCL21, CCL25, CCL27, CXCL12, CXCL13, CXCL-8, CCL2, CCL3, CCL4, CCL5, CCL11, CXCL10), lymphokines (e.g., granulocyte-macrophage colony-stimulating factor), and combinations thereof (including combinations with interferons).

Examples of monoclonal antibodies useful as a prophylactic or treatment for such subjects include, but are not limited to, bamlanivimab plus etesevimab, casirivimab plus imdevimab, sotrovimab, tixagevimab plus cilgavimab, or bebtelovimab.

The term "pharmaceutical composition", as used herein, represents a composition containing a compound described herein formulated with a pharmaceutically acceptable excipient, carrier, and/or diluent. In some embodiments, the pharmaceutical composition is manufactured or sold with the approval of a governmental regulatory agency as part of a therapeutic regimen for the treatment of disease in a mammal. The active agents disclosed herein combat viral infections, including but not limited to, coronavirus (e.g., HCoV-HKU1, HCoV-OC43, HCoV-NL63, HCoV-229E, MERS-CoV, SARS-CoV, and SARS-CoV-2 or 2019-CoV), and may be formulated in pharmaceutical compositions for any route of administration. Non-limiting exemplary routes of administration include oral, intradermal, transdermal (e.g., sustained release formulations), intramuscular, intraperitoneal, intravenous, subcutaneous, epidural, topical, injection, ocular, optic, nasal, nebulization, and inhalation routes. Any other route of administration that is therapeutically effective can be used. It can be used by gene therapy administered to a patient (e.g., via a vector). Furthermore, the proteins according to the disclosure can be administered together with other components of the active agents, such as pharmaceutically acceptable surfactants, excipients, carriers, diluents, and vehicles. For example, for oral administration, the pharmaceutical composition may be formulated in unit dosage form (e.g., a tablet, capsule, caplet, gel cap, lozenge). In certain embodiments, the pharmaceutical composition is formulated as an inhalable formulation, including but not limited to, a spray (e.g., an oral or nasal spray), a dry powder, an aerosol, a liquid, a gas, or atomizable particles or droplets. These formulations may be used in combination with nebulizers, inhalers (e.g., metered-dose inhalers, dry-powder inhalers), gas masks (e.g., SootherMask™; InspiraMask™; available from InspiRx, Inc.), or the like.

Useful pharmaceutical carriers, excipients, and diluents for the preparation of the compositions hereof, can be solids, liquids, or gases. These include any and all solvents, dispersion media, coatings, antibacterial and antifungal agents, isotonic and absorption delaying agents and the like. The pharmaceutically acceptable carrier or excipient does not destroy the pharmacological activity of the disclosed compound and is nontoxic when administered in doses sufficient to deliver a therapeutic amount of the compound. The compositions of the disclosure can take the form of powders, other formulations (e.g., packaging in lipid-protein vesicles), solutions, suspensions, elixirs, and aerosols. The carrier can be selected from the various oils including those of petroleum, animal, vegetable, or synthetic origin, e.g., peanut oil, soybean oil, mineral oil, and sesame oil. Water, saline, aqueous dextrose, and glycols are examples of liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, chitosan, talc, glucose, lactose, gelatin, malt, rice, flour, chalk, silica, magnesium stearate, sodium stearate, glycerol monostearate, sodium chloride, dried skim milk, glycerol, propylene glycol, water, and ethanol. The compositions may be subjected to conventional pharmaceutical additives such as preservatives, stabilizing agents, wetting or emulsifying agents, salts for adjusting osmotic pressure, and buffers. Suitable pharmaceutical carriers and their formulation are described in Remington's Pharmaceutical Sciences by E. W. Martin, incorporated herein in its entirety. Such compositions will, in any event, contain an effective amount of the active compound together with a suitable carrier so as to prepare the proper dosage form for administration to the recipient.

The active agents or compounds described herein may be present as a pharmaceutically acceptable salt. Typically, salts are composed of a related number of cations and anions (at least one of which is formed from the compounds described herein) coupled together (e.g., the pairs may be bonded ionically) such that the salt is electrically neutral. Pharmaceutically acceptable salts may retain or have similar activity to the parent compound (e.g., an $ED_{50}$ within 10%) and have a toxicity profile within a range that affords utility in pharmaceutical compositions. For example, pharmaceutically acceptable salts may be suitable for use in contact with the tissues of humans and animals without undue toxicity, irritation, allergic response and are commensurate with a reasonable benefit/risk ratio. Pharmaceutically acceptable salts are described in: Berge et al., J. Pharmaceutical Sciences 66:1-19, 1977 and in Pharmaceutical Salts: Properties, Selection, and Use, (Eds. P. H. Stahl and C. G. Wermuth), Wiley-VCH, 2008. Salts may be prepared from pharmaceutically acceptable non-toxic acids and bases including inorganic and organic acids and bases. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, dichloroacetate, digluconate, dodecylsulfate, ethanesulfonate, formate, fumarate, glucoheptonate, glutamate, glycerophosphate, hemisulfate, heptonate, hexanoate, hippurate, hydrobromide, hydrochloride, hydroiodide, 2-hydroxy-ethanesulfonate, isethionate, lactobionate, lactate, laurate, lauryl sulfate, malate, maleate, malonate, mandelate, methanesulfonate, mucate, 2-naphthalenesulfonate, nicotinate, nitrate, oleate, oxalate, palmitate, pamoate, pantothenate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative basic salts include alkali or alkaline earth metal salts include sodium, lithium, potassium, calcium, and magnesium, aluminum salts, as well as nontoxic ammonium, quaternary ammonium, and amine cations, including, but not limited to ammonium, tetramethylammonium, tetraethylammonium, methylamine, dimethylamine, trimethylamine, triethylamine, caffeine, and ethylamine.

As used herein, the terms "treatment", "treating", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. The term "prevent" or "prophylaxis" as used herein, includes delaying the onset of or progression of a disease or physiological manifestation of disease. The term "treat" includes reducing, diminishing, eliminating, ameliorating, forestalling, slowing the progression of, and/or delaying the onset of a given disease or physiological manifestation thereof.

Typically, the treatment of a condition (e.g., the viral respiratory infections and their conditions or symptoms described herein, e.g., coughing, fever, inflammation, fatigue, etc.) is an approach for obtaining beneficial or desired results including clinical results. Inflammation often occurs when tissues are injured by viruses, bacteria, trauma, chemicals, heat, cold, allergens, or any other harmful stimulus. Chemicals including bradykinin, histamine, serotonin and others are released, attracting tissue macrophages and white blood cells to localize in an area to engulf and destroy foreign substances. During this process, chemical mediators such as TNFα are released, giving rise to inflammation. Inflammatory disorders are those in which the inflammation is sustained or chronic. Beneficial or desired results to an inflammatory disease, condition, or disorder can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

Another aspect of the disclosure provides for the administration of a cytokine in a therapeutically effective amount in an amount of 1 picogram (pg)/milliliter (mL)-100 micrograms (μg)/mL (e.g., 100 pg/mL-50 μg/mL, 1 nanogram (ng)/mL-1 μg/mL, 10 ng/mL-100 ng/mL) and the therapeutic agent in a therapeutically effective amount in an amount of 1 μg/kg/day-1000 mg/kg/day (e.g., 10 μg/kg/day-750 mg/kg/day, 100 μg/kg/day-500 mg/kg/day, 500 μg/kg/day-100 mg/kg/day).

The pharmaceutical composition may be in unit dose form (e.g. spray, liquid, aerosol, dry powder, gas, atomizable particles or droplets). In certain embodiments the unit dose for comprises a cytokine in a therapeutically effective amount in an amount of 1 picogram (pg)/milliliter (mL)-100 micrograms (μg)/mL (e.g., 100 pg/mL-50 μg/mL, 1 nanogram (ng)/mL-1 μg/mL, 10 ng/mL-100 ng/mL) or alternatively, a cytokine may be 0.5 million international units (IU)-10 million IU (e.g., 1 million IU-8 million IU, 2 million IU-6 million IU) and the therapeutic agent in a therapeutically effective amount in an amount of 1 μg/kg/day-1000 mg/kg/day (e.g., 10 μg/kg/day-750 mg/kg/day, 100 μg/kg/day-500 mg/kg/day, 500 μg/kg/day-100 mg/kg/day). The dosages may be administered on a once or more weekly basis, or on a once or more daily basis, or the like as determined by a medical practitioner.

The pharmaceutical compositions of the present disclosure may also be in the form of an oral or nasal spray. The oral or nasal spray may be formulated such that each spray administers, for example, less than 100 μg/mL, less than 50 μg/mL, less than 1 microgram/mL, less than 100 ng/mL, or less than 100 pg/mL of cytokine. The oral, nasal, or inhaled spray may further comprise a therapeutic agent sprayed in an amount of less than 1000 mg/kg/day, less than 500 mg/kg/day, less than 50 mg/kg/day, less than 1 mg/kg/day, less than 100 μg/kg/day, less than 10 μg/kg/day, less than 1 μg/kg/day. The spray, liquid, aerosol, dry powder, gas, atomizable particles or droplets may be in a volume ranging from 1 ml to 50 ml and contain particles, comprising the pharmaceutical composition of the disclosure, in a particle size range of 0.5 μm-5 μm (e.g., as measured by dynamic light scattering), as these are sizes used for aerosols that are intended to be targeted into the lung or lower respiratory tract, which is useful for respiratory disease, conditions, or the like, including but not limited to viral respiratory infections. Another embodiment may utilize particle sizes in a range from greater than 5 μm (e.g., 10-100 μm, 10-50 μm, 10-30 μm) for optimal delivery to the nasal region or upper respiratory tract.

For monoclonal antibodies, pharmaceutical compositions comprise a prophylactically or therapeutically effective amount of an antibody or a fragment thereof, or a peptide immunogen, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences". Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, intrarectal, vaginal, topical or delivered by mechanical ventilation.

Active vaccines are also envisioned where antibodies like those disclosed are produced in vivo in a subject at risk of infection. Such vaccines can be formulated for parenteral administration, e.g., formulated for injection via the intradermal, intravenous, intramuscular, subcutaneous, or even intraperitoneal routes. Administration by intradermal and intramuscular routes are contemplated. The vaccine could alternatively be administered by a topical route directly to the mucosa, for example, by nasal drops, inhalation, by nebulizer, or via intrarectal or vaginal delivery. Pharmaceutically acceptable salts include the acid salts and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Passive transfer of antibodies, known as artificially acquired passive immunity, generally will involve the use of intravenous or intramuscular injections. The forms of antibody can be human or animal blood plasma or serum, as pooled human immunoglobulin for intravenous (IVIG) or intramuscular (IG) use, as high-titer human IVIG or IG from immunized or from donors recovering from disease, and as monoclonal antibodies. Such immunity generally lasts for only a short period of time, and there is also a potential risk for hypersensitivity reactions, and serum sickness, especially from gamma globulin of non-human origin. However, passive immunity provides immediate protection. The antibodies will be formulated in a carrier suitable for injection, i.e., sterile and syringeable.

Generally, the ingredients of compositions of the disclosure are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The methods of treating infections may further comprise other therapies. For example, the methods may include a second antiviral therapy such as a neuraminidase inhibitor, remdesivir, azithromycin, hemagglutinin inhibitor, nirmatrelvir with ritonavir, or molnupiravir. Other therapies included in the methods are medications that modulate the immune system or host cell factors such as dexamethasone, corticosteroids, an IL-6 inhibitor such as tocilizumab, an IL-1 inhibitor, or a kinase inhibitor such as baricitinib.

REFERENCES

1. Nowell P C. Phytohemagglutinin: An Initiator of Mitosis in Cultures of Normal Human Leukocytes. Cancer Research. 1960 May 1; 20(4):462-6.
2. Wheelock E F. Interferon-Like Virus-Inhibitor Induced in Human Leukocytes by Phytohemagglutinin. Science. 1965 Jul. 16; 149(3681):310-1.
3. Chen Y, Wang J, Liu C, Su L, Zhang D, Fan J, et al. IP-10 and MCP-1 as biomarkers associated with disease severity of COVID-19. Molecular Medicine. 2020 Oct. 29; 26(1):97.
4. Voloudakis G, Vicari J M, Venkatesh S, Hoffman G E, Dobrindt K, Zhang W, et al. A translational genomics approach identifies IL10RB as the top candidate gene target for COVID-19 susceptibility. npj Genom Med. 2022 Sep. 5; 7(1):1-15.
5. Riss T L, Moravec R A, Niles A L, Duellman S, Benink H A, Worzella T J, et al. Cell Viability Assays. In: Markossian S, Grossman A, Brimacombe K, Arkin M, Auld D, Austin C, et al., editors. Assay Guidance Manual [Internet]. Bethesda (Md.): Eli Lilly & Company and the National Center for Advancing Translational Sciences; 2004
6. Lalvani, A and Pathan, A inventors, Oxford University Innovation Ltd assignee. U.S. Pat. No. 9,005,902 Tuberculosis diagnostic test. 2015

What is claimed:

1. A method of determining innate immune response to a viral infection of a subject comprising:

(a) mixing a subject blood sample comprising plasma with an anticoagulant solution;

(b) separating the mixture of step (a) into two or more sample mixtures;

(c) adding a sample of innate immune cells incubated with one or more lectins selected from the group consisting of phytohemagglutinin, concanavalin A, lentil lectin, snowdrop lectin, ricin, peanut agglutinin, jacalin, hairy vetch lectin, wheat germ agglutinin, elderberry lectin, *Maakia amurensis* leukoagglutinin, *Maakia amurensis* hemagglutinin, *Ulex europaeus* agglutinin, *Aleuria aurantia* lectin, and a combination thereof to a first sample mixture of step (b) to form a cell sample aliquot;

(d) adding a sample of innate immune cells not incubated with one or more lectins selected from the group consisting of phytohemagglutinin, concanavalin A, lentil lectin, snowdrop lectin, ricin, peanut agglutinin, jacalin, hairy vetch lectin, wheat germ agglutinin, elderberry lectin, *Maakia amurensis* leukoagglutinin, *Maakia amurensis* hemagglutinin, *Ulex europaeus* agglutinin, *Aleuria aurantia* lectin, and a combination thereof to a second sample mixture of step (b) to form a control sample aliquot;

(e) incubating the cell sample aliquot and the control sample for at least one hour at a temperature in a range of about 36.1° C. to about 37.2° C.;

(f) separating the plasma from the innate immune cells in the cell sample aliquot to form a plasma cell sample;

(g) separating the plasma from the innate immune cells in the control sample aliquot to form a plasma control sample;

(h) measuring one or more cytokines in the plasma cell sample and one or more cytokines in the plasma control sample;

(i) calculating a net stimulation of cytokines in the cell sample aliquot by subtracting the concentration of cytokines in the control sample aliquot from the concentration of cytokines in the cell sample aliquot; and (j) comparing the net stimulation to a reference group of subjects having adequate innate immunity reactivity to the viral infection that limits viral invasion in early infection of the viral infection to determine the innate immune response to a viral infection of the subject.

2. The method of claim 1, wherein the one or more cytokines are one or more interferons, one or more interleukins, one or more tumor necrosis factors, one or more chemokines, one or more lymphokines, or a combination thereof.

3. The method of claim 2, wherein the one or more interferons are IFN-α, INF-β, INF-γ, IFN-ε, IFN-κ, IFN-ω, IFN-δ, IFN-τ, IFN-ζ, INF-λ, or a combination thereof.

4. The method of claim 1, comprising the further step after step (a) and before step (b) of dividing the mixture of step (a) into a second mixture and adding a sample of lectin-free innate immune cells to the second mixture to form a control cell sample aliquot.

5. The method of claim 4, wherein step (f) comprises comparing the measurement of the one or more cytokines in the plasma of the cell sample aliquot with a measurement of one or more cytokines in the plasma of the control aliquot.

6. A method of treating a subject having an innate immune response to a viral infection comprising:

(a) mixing a subject blood sample comprising plasma with an anticoagulant solution;

(b) separating the mixture of step (a) into two or more sample mixtures;

(c) adding a sample of innate immune cells incubated with one or more lectins selected from the group consisting of phytohemagglutinin, concanavalin A, lentil lectin, snowdrop lectin, ricin, peanut agglutinin, jacalin, hairy vetch lectin, wheat germ agglutinin, elderberry lectin, *Maakia amurensis* leukoagglutinin, *Maakia amurensis* hemagglutinin, *Ulex europaeus* agglutinin, *Aleuria aurantia* lectin, and a combination thereof to a first sample mixture of step (b) to form a cell sample aliquot;

(d) adding a sample of innate immune cells not incubated with one or more lectins selected from the group consisting of phytohemagglutinin, concanavalin A, lentil lectin, snowdrop lectin, ricin, peanut agglutinin, jacalin, hairy vetch lectin, wheat germ agglutinin, elderberry lectin, *Maakia amurensis* leukoagglutinin, *Maakia amurensis* hemagglutinin, *Ulex europaeus* agglutinin, *Aleuria aurantia* lectin, and a combination thereof to a second sample mixture of step (b) to form a control sample aliquot;

(e) incubating the cell sample aliquot and the control sample for at least one hour at a temperature in a range of about 36.1° C. to about 37.2° C.;

(f) separating the plasma from the innate immune cells in the cell sample aliquot to form a plasma cell sample;

(g) separating the plasma from the innate immune cells in the control sample aliquot to form a plasma control sample;

(h) measuring one or more cytokines in the plasma cell sample and one or more cytokines in the plasma control sample;

(i) calculating a net stimulation of cytokines in the cell sample aliquot by subtracting the concentration of cytokines in the control sample aliquot from the concentration of cytokines in the cell sample aliquot;

(i) comparing the net stimulation to a reference group of subjects having adequate innate immunity reactivity to the viral infection that limits viral invasion in early infection of the viral infection; and (k) administering a therapeutic to the subject identified as having the innate immune response to the viral infection.

7. The method of claim 6, wherein the therapeutic is one or more cytokines, one or more antibodies, antivirals, or a combination thereof.

8. The method of claim 7, wherein the one or more cytokines is one or more interferons, one or more interleukins, one or more tumor necrosis factors, one or more chemokines, one or more lymphokines, or a combination thereof.

9. The method of claim 8, wherein the one or more interferons are IFN-α, INF-β, INF-γ, IFN-ε, IFN-κ, IFN-ω, IFN-δ, IFN-τ, IFN-ζ, INF-λ, or a combination thereof.

10. The method of claim 8, wherein the one or more interleukins are IL-1, IL-2, IL-3, IL-4, IL-5, IL-6, IL-7, IL-8, IL-9, IL-10, IL-11, IL-12, IL-13, IL-14, IL-15, IL-16, IL-17, or a combination thereof.

11. The method of claim 8, wherein the one or more tumor necrosis factors are TNFα, TNFβ, TNFγ, or a combination thereof.

12. The method of claim 8, wherein the one or more chemokines are CCL14, CCL19, CCL20, CCL21, CCL25, CCL27, CXCL12, CXCL13, CXCL-8, CCL2, CCL3, CCL4, CCL5, CCL11, CXCL10, or a combination thereof.

13. The method of claim 8, wherein the one or more lymphokines is granulocyte-macrophage colony-stimulating factor.

14. The method of claim 7, wherein the one or more antibodies are bamlanivimab plus etesevimab, casirivimab plus imdevimab, sotrovimab, tixagevimab plus cilgavimab, tocilizumab, or bebtelovimab.

15. The method of claim 7, wherein the one or more antivirals are neuraminidase inhibitor, remdesivir, azithromycin, hemagglutinin inhibitor, nirmatrelvir with ritonavir, molnupiravir, or a combination thereof.

16. The method of claim 1, wherein the viral infection is a coronavirus infection.

17. The method of claim 6, wherein the viral infection is a coronavirus infection.

* * * * *